US00PP11499P

United States Patent [19]

Olesen et al.

[11] Patent Number: Plant 11,499

[45] Date of Patent: Sep. 5, 2000

[54] MINIATURE ROSE PLANT NAMED 'POULRAEL'

[75] Inventors: L. Pernille Olesen; Mogens N. Olesen, both of Fredensborg, Denmark

[73] Assignee: Poulsen Roser Aps, Fredensborg, Denmark

[21] Appl. No.: 09/122,436

[22] Filed: Jul. 24, 1998

[51] Int. Cl.[7] ..... A01H 5/00

[52] U.S. Cl. ..... Plt./116

[58] Field of Search ..... Plt./116, 117, 118, Plt./119, 121

[56] References Cited

U.S. PATENT DOCUMENTS

P.P. 10,934 6/1999 Olesen et al. ..... Plt./121

*Primary Examiner*—Howard J. Locker

[57] ABSTRACT

A new miniature pot rose plant which has abundant champagne-colored flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE DISCOVERY

The present discovery constitutes a new and distinct variety of miniature rose plant which was discovered in a cultivated area. The mutation resulted from POULlak, a variety by the same inventors described and illustrated in U.S. Plant Pat. No. 10,934 filed Mar. 21, 1997. The new rose variety resulted from a naturally occurring mutation of unknown causation on a branch of 'POULlak' which was discovered in a controlled planting.

The rose plant of the present discovery has a unique combination of characteristics which are outstanding in the new variety and which distinguish it from the original rose 'POULlak' as well as all other varieties which we are aware of. For example, the new variety has:

1. Abundant, champagne colored flowers;
2. Attractive long lasting foliage and compact growth,
3. Year-round flowering under glasshouse conditions;
4. Suitability for production from softwood cuttings in pots;
5. Durable flowers and foliage which make the variety suitable for distribution in the floral industry.

This combination of qualities was not present in previously available commercial cultivars of this type and dintinguish 'POULrael' from all other varieties of which we are aware.

The resulting mutation was evaluated and trials were conducted of the resulting rose plants in a controlled environment.

Asexual reproduction of 'POULrael' by cuttings was first done by L. Pernille and Mogens N. Olesen in their nursery in Fredensborg, Denmark in March, 1996. This initial and other subsequent propagations have demonstrated that the characteristics of 'POULrael' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULrael'. Specifically illustrated in SHEET 1:

1. Stem or entire plant showing branching and the attachment of leaves, buds, and peduncles;

2. Flower bud, partially opened bud, and open bloom;
3. Flower petals, detached;
4. Sepals, receptacle, and pedicel;
5. Flowering stem as well as a bare stem exhibiting thorns;
6. Leaves.

DETAILED DESCRIPTION OF THE VARIETY

The following is a detailed description of 'POULrael', as observed in its growth in glasshouses in Fredensborg, Denmark and Half Moon Bay, Calif. and in field nursery in Jackson County, Oreg. Color references are made using The Royal Horticultural Society (London, England) Colour Chart, 1995, except where common terms of color are used.

For a comparison, the nearest existing rose variety is 'POULlak', a patented variety described and illustrated in U.S. Plant Pat. No. 10,934. Chart 1 details several physical charcteristics of 'POULrael' and 'POULlak'.

CHART 1

| | 'POULrael' | 'POULlak' |
|---|---|---|
| Bud color at ¼ open | Yellow-White Group 158D | Red Group 39D |
| Upon opening, color of upper surface of petal | Outermost petals: Orange Group 27D<br>Innermost petals: Red Group 36A | Red Group 49A |
| Basal petal spot | Outermost petals: Yellow Group 4B–4C<br>Innermost petals: Yellow Group 4A | Outmost petals: Yellow Group 3D<br>Innermost petals: Yellow Group 3D |

Parentage: Mutation of 'POULlak'.

Classification:

*Botanical.*—*Rosa hybrida.*

*Commercial.*—Miniature.

FLOWER AND FLOWER BUD

Blooming habit: Continuous.

Flower bud:

*Size.*—Upon opening, 12–16 mm in length from base of receptacle to end of bud.

*Bud form.*—Pointed ovoid.

*Bud color.*—As sepals unfold, Red Group 36 C. Yellow-White Group 158D at ¼ opening.

*Sepals.*—Green Group 143A. Weak foliaceous appendages and stipitate glands on three of the five sepals. Some flowers lacking appendages on sepals.

*Peduncle.*—Surface: Generally smooth, some hairs present. Length: 25–35 mm average length. Color: Green Group 143A. Strength: Erect.

*Receptacle.*—Surface: Smooth. Shape: Funnel-shaped. Size: Small 4 mm (h)×5 mm (w). Color: Green Group 143A.

*Borne.*—Generally multiple buds with 2–4 flower buds per flowering stem.

Flower bloom:

*Size.*—Small for a 10 cm pot rose. Average diameter is 35 mm when open.

*Form.*—Shape of flower when viewed from the side: Upon opening, upper part: Flat to cupped. Upon opening, lower part: Convex. Open flower, upper part: Flattened convex. Open flower, lower part: Flattened convex.

*Petalage.*—Very double. Average range: 55–65 petals under normal conditions.

*Color.*—Upon opening, the upper surface of the outermost petals is Orange Group 27D. The upper surface of the innermost petals is Red Group 36A. Upon opening, the reverse surface of the outermost petals is Yellow-White Group 158D to Orange-White Group 159D. The reverse surface of the innermost petals is Red Group 36B. After opening, the upper surface of the outermost petals is Yellow-White Group 158D. After opening, the upper surface of the innermost petals is Red Group 36C. After opening, the reverse surface of the outermost petals is Yellow-White Group 158D. After opening, the reverse surface of the innermost petals is Red Group 36C. Upon opening, a petal spot Yellow Group 4B to 4C exists on the inner and outer bases of the outermost petals. Upon opening, a petal spot Yellow Group 4A exists on the inner and outer bases of the innermost petals. After opening, the petal spot is Yellow Group 4C to 4D on the inner and outer bases of the outermost petals. After opening, the petal spot is Yellow Group 4A on the inner and outer bases of the innermost petals.

General tonality: Between day 6 and 8 the overall tonality is a blend of Orange Group 27D and Red Group 36D.

*Petal reflex.*—Outermost petals are double reflexed. Innermost petals reflex backwards slightly.

*Petaloids.*—Commonly none.

*Fragrance.*—Light floral scent.

*Duration.*—As a pot plant, flowers last from 16 to 18 days. As a cut flower 8 to 12 days.

Petals:

*Texture.*—Average.

*Shape.*—Oval.

*Arrangement.*—Normal.

*Petal edge.*—Some petal margins pointed.

Reproductive organs:

*Pollen.*—Some flowers lacking complete floral parts. Abundance: Limited. Color: Yellow Group 13A.

*Anthers.*—Size: Small. Color: Yellow Group 13A. Mature Color: Brown Group 200C.

*Filaments.*—Color: Yellow Group 1A.

*Stigmas.*—Positioned slightly superior to anthers. Color: Green-White Group 157C.

*Styles.*—Color: Green-White Group 157C.

PLANT

Plant growth: Compact and vigorous. Upright to bushy. When grown as a 10 cm pot plant, the average height of the plant itself is 18–20 cm and the average width is 20–22 cm. When grown as a nursery plant on its own roots the average plant height is 25–35 cm and the average plant width is 25–35 cm.

Stems:

*Color.*—Young wood: Green Group 138B. Older wood: Green Group 138B.

*Prickles.*—Incidence: Moderate number. Size: Average length: 3 mm–4 mm. Color: Yellow-Green Group 145D. Shape: Straight to slightly curved.

*Bark.*—Young wood: Smooth. Older wood: Smooth.

Plant foliage: Normal number of leaflets on normal leaves in middle of the stem: 5 leaflets. Some leaves with 3 leaflets.

*Leaf size.*—Small. 60 mm (l)×35 mm (w).

*Abundance.*—Above average.

*Color.*—Upper Leaf Surface: Green Group 137A. Lower Leaf Surface: Green Group 138B. Juvenile Foliage: Green Group 143A.

Plant leaves and leaflets:

*Stipules.*—Present. Margins with hairs. Size: 8 mm–10 mm Color: Green Group 137C.

*Petiole.*—Length: 16 mm–18 mm. Underneath: Smooth. Some with prickles. Color: Green Group 137B.

*Rachis.*—With hairs and prickles. Color: Green Group 137B.

*Leaflet edge.*—Finely serrated.

*Shape.*—Leaflets are ovate.

*Leaflets.*—Number: 5

*Other.*—Matte finish. Thin texture.

Disease resistance: Above average resistance to mildew and Botrytis under normal growing conditions in Half Moon Bay, Calif. and Fredensborg, Denmark.

We claim:

1. A new and distinct variety of rose plant of the miniature class, substantially as herein illustrated and described as a distinct and novel rose variety due to its abundant champagne-colored flowers, vigorous and compact growth, year-round flowering under glasshouse conditions, suitability for production from softwood cuttings in pots, and durable flowers and foliage which make the variety suitable for distribution in the floral industry.

* * * * *

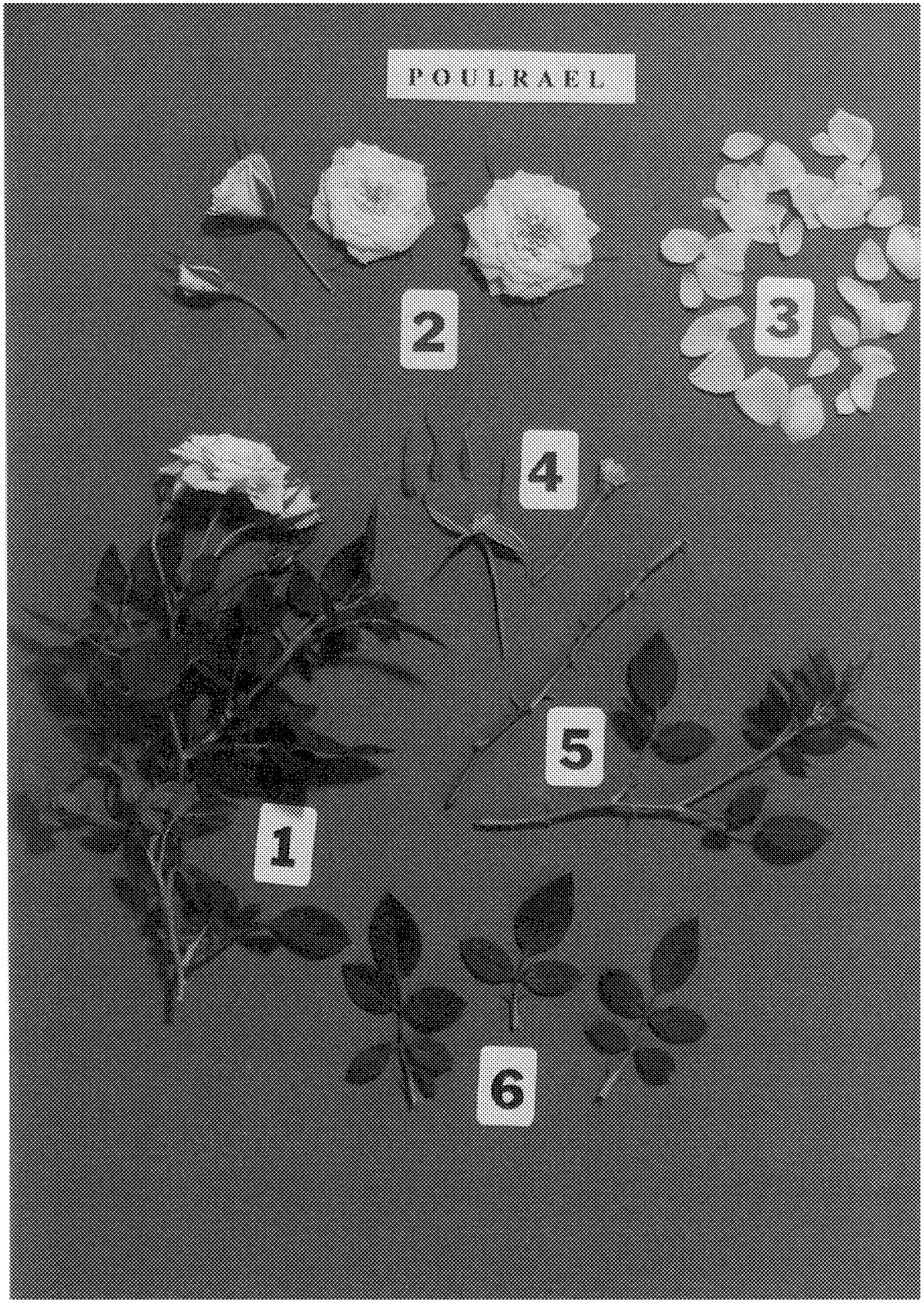
POULRAEL
2
3
4
5
1
6